United States Patent

Lansink-Rotgerink et al.

[11] Patent Number: 5,919,566
[45] Date of Patent: *Jul. 6, 1999

[54] INORGANIC SUPPORT MATERIALS CONTAINING SULPHONATE AND MERCAPTO GROUPS, PROCESS FOR THE PRODUCTION THEREOF AND USE AS CATALYST

[75] Inventors: Hans Lansink-Rotgerink, Glattbach; Stefan Wieland, Offenbach; Emmanuel Auer, Frankfurt, all of Germany

[73] Assignee: Degussa Aktiengesellschaft, Frankfurt am Main, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/731,734

[22] Filed: Oct. 21, 1996

[30] Foreign Application Priority Data

Oct. 31, 1995 [DE] Germany ............... 195 40 497

[51] Int. Cl.$^6$ ...................................... B32B 5/16
[52] U.S. Cl. ............... 428/405; 428/447; 528/30
[58] Field of Search ..................... 428/405, 447

[56] References Cited

U.S. PATENT DOCUMENTS

| | | | |
|---|---|---|---|
| 3,172,916 | 3/1965 | Wagner | 260/619 |
| 4,005,046 | 1/1977 | Chandra et al. | 252/428 |
| 4,257,916 | 3/1981 | Hancock et al. | 252/430 |
| 4,374,263 | 2/1983 | Hancock et al. | 560/204 |
| 4,918,245 | 4/1990 | Iimuro et al. | 568/727 |
| 5,096,733 | 3/1992 | Vallyathan et al. | 427/2 |
| 5,153,068 | 10/1992 | Kohara et al. | 428/405 |
| 5,298,665 | 3/1994 | Janssen et al. | 568/342 |
| 5,354,831 | 10/1994 | Panster et al. | 528/9 |
| 5,380,791 | 1/1995 | Panster et al. | 524/837 |

FOREIGN PATENT DOCUMENTS

| | | |
|---|---|---|
| 0028107 | 5/1981 | European Pat. Off. . |
| 0319327 | 6/1989 | European Pat. Off. . |
| 0582811 | 2/1994 | European Pat. Off. . |
| 0693470 | 1/1996 | European Pat. Off. . |
| 1 506 226 | 4/1978 | United Kingdom . |
| 1506226 | 4/1978 | United Kingdom . |

*Primary Examiner*—Margaret W. Glass
*Attorney, Agent, or Firm*—Beveridge, DeGrandi, Weilacher & Young, L.L.P.

[57] ABSTRACT

Inorganic support materials containing sulphonate and mercapto groups, and a process for the modification of these materials with the corresponding difunctional organosilicon compounds and use thereof as catalysts in acid-catalyzed reactions.

8 Claims, No Drawings

INORGANIC SUPPORT MATERIALS CONTAINING SULPHONATE AND MERCAPTO GROUPS, PROCESS FOR THE PRODUCTION THEREOF AND USE AS CATALYST

INTRODUCTION AND BACKGROUND

The present invention relates to oxide and silicate based solids modified on the surface with bifunctional organosilicon compounds containing sulphur. In another aspect, the present invention relates to a process for producing modified inorganic support materials and to the use thereof as catalysts.

Treating such inorganic solids with organosilicon compounds is well known in the prior art. For example, polysulphanes (U.S. Pat. No. 4,514,231, German patent 33 14 742) or polyether-substituted silicon compounds (U.S. Pat. No. 4,151,154) are known for this purpose.

The problem underlying these patents, however, resided in determining how to improve the incorporability of inorganic fillers into rubber compounds and which rubber properties would simultaneously change advantageously as a result of such incorporation.

Sulphonic acid organic ion exchangers are known from the prior art which are modified with compounds containing sulphur, in particular containing mercapto groups, in order to increase the activity and selectivity thereof as condensation catalyst (EP A 0 630 878). However, a risk arises in the case of a compound containing sulphur becoming detached from the surface, thereby degrading the characteristics of the corresponding catalyst (EP A 0 583 712). Another disadvantage of this type of catalyst is that it must be pre-swollen before being used, for example, in bishpenol A synthesis.

In contrast, an object of the present invention is to provide solids which have both sulphonate or sulphonic acid groups and mercapto groups on the surface and which may be used as catalysts, for example, in condensation reactions without the risk associated with prior developments.

SUMMARY OF THE INVENTION

In achieving the above and other objects, one feature of the present invention provides inorganic support material of a wide variety that is chemically modified, and more particularly, oxide and silicate based solids modified on the surface with bifunctional organosilicon compounds.

The organosilicon compounds used for the modification are of the formula $$[(RO)_y Si-R^1-SO_3^-]_x M^{x+} \quad (I)$$

and of the formula $$(RO)_y Si-R^2-SH \quad (II)$$

in which:

R$^1$ is linear or branched alkylene having 1 to 12 C atoms, cycloalkylene having 5 to 8 C atoms or a unit of the formulae

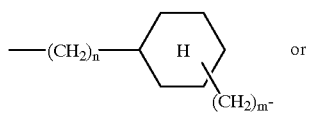

or

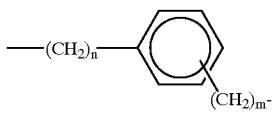

in which n or m is a number from 0 to 6 and states the number of methylene groups in the silicon or sulphur position, M equals H$^+$ or optionally also NH$_4$+ or a metal ion having a valency of x equals 1 to 4, wherein H$^+$ is always present in an amount of at least 5% of the ion exchange capacity of (I), y is an integer from 1 to 3, preferably 3, R$^2$ is identical or different from R$^1$ and also has the same meanings as R$^1$ above R is identical or different and is methyl, ethyl, propyl or H A prerequisite for the production of the modified solids according to the invention is the presence of OH groups on the surface of the solids that are modified. These OH groups react with the alkoxy groups of the compounds according to the formulae (I) and (II), thereby bonding the catalytically active groups SO$_3^-$M$^{x+}$ and SH onto the surface of the oxide or silicate solid, where M$^{x+}$ preferably means H$^+$.

For this reason, the total number of reactable alkoxy groups of the compounds (I) and (II) will not generally exceed the number of reactable OH groups on the surface of the oxide or silicate solid. However, for certain applications, a certain percentage (1–30%) of the reactable OH groups is deliberately retained. The term "surface" here includes any surfaces of the solid including, for example, those located within moldings of the most varied type, in particular surfaces inside of pores.

Another feature of the invention provides a process for the production of solids according to the above structure.

In carrying out this aspect of the invention a multi-stage process is followed; that is:

a) the solid in the form of moldings of the support material is optionally impregnated by immersion or spraying with a compound of the general formula (IV)

$$Me(OR)_{2-4}R_{0-2} \text{ or } Me(OR)_{2-3}R_{0-1} \quad (IV),$$

in which

Me is Si, Ti, Al

R has the above meaning;

after being separated from any possible liquid phase, the solid is dried at 60 to 140° C. and b) the support material is reacted at a temperature of 20 to 140° C. with an aqueous solution of organosilicon compounds according to the formula (I) by immersion in a solution thereof or by spraying with a solution thereof at standard pressure or pressure corresponding to the sum of the partial pressures prevailing at the particular temperature, to thereby impregnate the support material, the impregnated support material is then separated and dried at 60 to 140° C., optionally hydrothermally post-treated and c) the resultant support material is further impregnated with a solution of an organosilicon compound according to the formula (II) or with the compound itself by immersion or spraying at 40–90° C. and the resultant material, after an optional washing operation with an aliphatic alcohol, is dried at temperatures of between 0 and 250° C.

The moldings referred to herein are shaped bodies of the oxide or silicate materials that are to be modified in accordance with the present invention. Any desirable shape can be selected; e.g. pellet, sphere or bead.

DETAILED DESCRIPTION OF THE INVENTION

In general, the process of the invention is carried out by selecting the molar ratio of the compounds according to the formulae (I) and (II) such that, when measured by the $SO_3^-$ and SH groups, the molar ratio is from 1:100 to 100:1, in particular from 1:10 to 10:1, preferably from 1:3 to 3:1 on the surface. The exact ratio in a particular case is also determined by the intended application of the catalyst.

Preferred compounds of formula I and II used to carry out the process according to the invention include those in which $R^1$ and $R^2$ have the same meaning and denote propylene and $M^{x+}$ and R in the formula (I) preferably mean $H^+$ and H respectively.

In another embodiment, 10 to 90 mol. % of the $SO_3$ groups are neutralized by alkali metal cations.

Suitable oxide and suitable silicate based solids that can be modified in accordance with the present invention can be of a natural or synthetic nature. Natural solids in particular also include clays. Preferred solids are synthetically produced silicas, whether pyrogenic or precipitated or in particular obtained by the sol/gel process, as well as aluminum oxide, titanium dioxide, zirconium dioxide together with mixed oxides of the stated compounds. These solids are initially preferably in finely divided form and then for the modification steps they are processed according to conventional technique into the shaped molding that is determined to be best suited for the intended end use as a catalyst.

It is, therefore, particularly preferred to react the moldings, obtained for example by pelletizing, extrusion or tabletting, with the compounds according to the formulae (I) and (II).

In particular cases, if the shaped moldings have proved, for example, to have inadequate abrasion resistance, these support materials are treated with compounds according to the formula

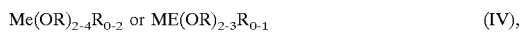

$$Me(OR)_{2-4}R_{0-2} \text{ or } ME(OR)_{2-3}R_{0-1} \qquad (IV),$$

in which

Me means Si, Ti, Al

R has the above meaning or the solutions thereof in water, ethyl alcohol or methyl alcohol. In particular tetraorthosilicate or the commercially available oligomer tetraethyl orthosilicate 40 are useful for this purpose (TES 40; $SiO_2$ is formed from the oligomer in the event of complete hydrolysis). The quantity of $SiO_2$ formed is 40 wt. % of the introduced quantity of TES 40. Aluminates or titanates unsubstituted or substituted by alkyl groups (1 to 3 C atoms) may also be used in the same manner. These compounds, which are described as non-functional silanes, aluminates or titanates are optionally used in a concentration of 0 to 50 wt. %, relative to the quantity of solid, preferably of 1 to 20 wt. %.

In a particularly suitable embodiment, this treatment proceeds as an optional pre-treatment before, or at the same time as, the surface modification of the solid with at least one of the compounds according to the formulae (I) or (II).

If the treatment of the solids in molded form with the compounds according to the formula (IV) is considered necessary, these compounds are generally introduced into a vessel in the form of a suitable solution, and the solid to be treated is mixed in. The resulting suspension is heated with stirring to temperatures of between 40 and 90° C., preferably 60 to 80° C. After a time of 10 minutes to 4 hours, the solid is separated from the fines (abraded material or hydrolized oxide, for example $SiO_2$ when tetraethyl silicate is used) and the resultant pre-treated solid is optionally further processed after drying at 60 to 140° C., preferably 100 to 130° C.

The concentration of compounds according to the formula IV in the solution or suspension generally ranges from 1 to 40 wt. %, relative to the solids used, and depending upon the stability of the moldings used.

The first stage of the process as described above with treatment by compounds of formula IV may be omitted for stable, strong moldings. This stage may in any case also be combined with the otherwise separately performed second stage by adding the compounds according to the formula (I) and/or formula (II) to the alcoholic solution of (IV) and treating the solid as herein described.

In another variant, however, surface modification proceeds after the first stage a) of the process in a second stage b) in which a compound according to the formula (IV) is again optionally introduced in addition to a compound according to the formula (I), preferably in the form of an aqueous or alcoholic solution.

In this case, the molar ratio of the sulphonate and mercapto groups ranges between 100:1 and 1:100, preferably between 10:1 and 1:10, in particular between 1:3 and 3:1. Modification is performed by spraying the solution(s) or also by immersing the moldings in such (a) solution(s). The temperature during modification is between 20° C. and 140° C., in particular between 20 and 100° C., wherein the pressure corresponds to the sum of the partial pressures prevailing at the particular pressure or to standard pressure. Hydrothermal treatment, as known from the prior art, is then optionally performed.

The solid support material treated in this manner is either used directly for the further impregnation stages (coating) with organosilicon compounds according to the formula (II), which are not generally soluble in an aqueous medium, or alternatively dried beforehand, generally at temperatures of 70 to 150° C.

The support material obtained in this manner is coated with the organosilicon compounds according to the formula (II) either by spraying with these compounds, optionally diluted with an organic solvent, in particular an alcohol having 1–3 C atoms, or by immersion in a corresponding solution of these compounds or the compounds themselves. In either case, care must be taken to ensure sufficiently thorough mixing.

After the reaction at 20 to 60° C., the resultant material is optionally washed, for example with the stated alcohols, in order to remove any excess, unreacted organosilicon compounds and then dried at temperatures of between 70 and 150° C., optionally of up to 250° C.

If it is decided to spray the support material either with the pure substances or with solutions thereof, it is left to the discretion of the person skilled in the art to determine, for example in the presence of moldings, how vigorously the mixing should be performed with regard to the stability of the moldings.

Methods are also, for example, technically feasible in which mixing or homogenization is performed in a first stage and the homogenized mixture is then subjected to the actual reaction, for example in another preheated mixer.

In another variant, the organosilicon compounds according to the formulae (I) or (II) may also be applied simultaneously onto the support material. In this case, an alcoholic aqueous solution optionally containing a known emulsifier is preferably used.

In any event the concentration of the two compounds during modification is adjusted in such a manner that they are present on the material to be modified in a molar ratio of preferably 1:10 to 10:1, in particular of 1:3 to 3:1.

The total content of the organosilicon compounds according to the formulae (I) or (II) then generally ranges from 0.1 to 70 wt. %, preferably from 1 to 10, relative to the solid.

Total sulphur content or also the acid capacity determined by titrating the sulphonic acid groups and the mercapto group content, which is the difference from the total sulphur content are of vital significance to catalytic properties.

The solids according to the invention have proved to be effective condensation catalysts for acid-catalyzed reactions. In particular, elevated levels of conversion and selectivity are achieved when they are used for the synthesis of bisphenol A.

The following examples illustrate the present invention.

EXAMPLE 1

700 ml (350 mmol) of a 0.5M aqueous solution of $(HO)_3Si-CH_2CH_2CH_2SO_3H$ (3-trihydroxysilylpropylsulphonic acid) and 76 g of tetraethyl orthosilicante 40 ("TES 40", precondensed tetraethyl orthosilicate, corresponding to the formation of 505 mmol of $SiO_2$) are introduced into a 3 liter double jacketed glass vessel and heated to 80° C. 200 g of $SiO_2$ support (grade C 15, Grace) are apportioned and reacted with the salane mixture for 3 hours with careful stirring. The impregnated solid beads are then separated from the fines (abraded material or hydrolized $SiO_2$), the impregnated $SiO_2$ beads washed twice with water and filtered and then dried for 12 hours under a nitrogen atmosphere at 135° C. 223 g of a glossy, spherical solid are isolated. An acid capacity of 0.25 mmol/g of solid is determined by titrating the solid with a 1 n sodium hydroxide solution against phenolphthalein. A sulphur content of 1.7% is determined by elemental analysis.

50 g of the support containing sulphonic acid groups pretreated in this manner are then introduced into ethanol and combined with four times the quantity, relative to the sulphonic acid groups present, of mercaptopropyltrimethoxysilane (50 mmol corresponding to 9.8 g) and refluxed for 3 hours while being stirred. The solid is then isolated by filtration (no further abraded material was found) and washed with ethanol. Once the material has been dried under nitrogen at 135° C. for a period of 12 hours, 55 g of product are obtained having a sulphur content of 3.3 wt. % (increase in sulphur content by 1.6%, corresponding to 57% of theoretical).

EXAMPLE 2

300 g of spherical γ-aluminum oxide (diameter 1.7–2.3 mm; BET surface area 185 m²/g; pore volume 0.6 ml/g) are introduced into a rotating container (mixer) and sprayed with 180 ml (144 mmol) of a 0.8 molar aqueous solution of $(HO)_3Si-CH_2CH_2CH_2SO_3H$ (3-trihydroxysilylpropylsulphonic acid). Spraying lasts 30 minutes, whereupon the pellets are dried at 120° C. under a vacuum. The resultant 325 g of pretreated support are then sprayed in a rotating container with 100 ml of an ethanolic solution of mercaptopropyltriethoxysilane (28.6 g, corresponding to 120 mmol, dissolved in 71 ml of ethanol) and dried again at 120° C. under a vacuum. 340 g of a glossy, highly abrasion resistant, spherical material are obtained.

Sulphur content (theoretical value in brackets): 2.3% (2.5%)

Acid capacity (theoretical value in brackets) 0.4 mmol/g (0.42 mmol/g)

EXAMPLE 3

200 g of shaped $TiO_2$ are treated as described in Example 1. The following analytical values are determined from the isolated solid:

Sulphur content: 1.2%

Acid capacity: 0.01 mmol/g

EXAMPLE 4

In a stirred apparatus, 10 g of an $SiO_2$ support (Grace C15) impregnated with sulphonic acid and mercapto groups and dried, which is produced as described in Example 1, are stirred with 70.58 g (0.75 mol) of phenol and 4.36 g (0.075 mol) of acetone until acetone conversion of 99% is reached. The yield of p/p-bisphenol A, determined by gas chromatography, is 96.4% at a selectivity for p/p-bisphenol A of 97.2% relative to the phenol used.

EXAMPLE 5

A cylindrical reactor (diameter 45 mm×length 170 mm) is filled with 100 g of a Grace grade C15 $SiO_2$ support impregnated as described in Example 1 and 50 g/h of a phenol/acetone mixture in a molar ratio of 10:1 are passed through. At a WHSV of 0.3 $h^{-1}$, acetone conversion is 96.9%, the yield of p/p-bisphenol A is 93.8% and the selectivity for p/p-bisphenol A, relative to phenol, is 95.5%. The quantity of non-isomerisable by-products is less than 0.1%.

Further variations and modifications of the foregoing will be apparent to those skilled in the art and are intended to be encompassed by the claims appended hereto.

German priority application 195 40 497.1 is relied on and incorporated herein by reference.

We claim:

1. A process for the production of an oxide or silicate based solid support material modified on the surface by reaction with a bifunctional organosilicon compound represented by the formula:

$$((RO)_y Si-R^1-SO_3^-)_x M^{x+} \qquad (I)$$

and by reaction with a bifunctional organosilicon compound represented by the formula:

$$(RO)_y Si-R^2-SH \qquad (II)$$

in which

R¹ is linear or branched alkylene having 1 to 12 C atoms, or a unit of the formulae:

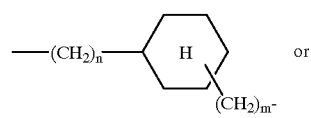

-continued

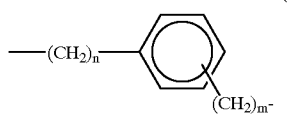
(III)

in which n and m each is a number from 0 to 6 and is the number of methylene groups attached to the silicon or sulphur respectively, M is $H^+$ or $NH_{4+}$ or a metal ion having a valency of x equal to 1 to 4, wherein $H^+$ is always present in an amount of at least 5% of the ion exchange capacity of (I), y is 3

$R^2$ is identical or different from $R^1$ and has the same meaning as $R^1$ above R is identical or different and is methyl, ethyl, propyl or H, said process comprising:

a) impregnating the solid support material by immersion or spraying with a compound of the formula $$Me(OR)_{2-4}R_{2-4}R_{0-2} \text{ or } Me(OR)_{2-3} R_{0-1} \qquad (IV)$$

in which Me is Si, Ti, wherein the total valence is 4, or Al, where the total valence is 3, and R has the above meaning, then separating from any possible liquid phase, and drying the solid at 60 to 140° C. and b) reacting the support material at a temperature of 20 to 140° C. with an aqueous solution of organosilicon compounds according to formula (I) by immersion in the solution or by spraying therewith at standard pressure or a pressure corresponding to the sum of the partial pressures prevailing at the particular temperatures, separating the resulting impregnated support material and drying at 60 to 140° C., optionally hydrothermally post-treating said material and c) impregnating the resultant support material with a solution of an organosilicon compound according to the formula (II) or with the compound itself by immersion or spraying at 40–90° C., optionally washing with an aliphatic alcohol, and drying at temperatures of between 70 and 250° C.

2. The process according to claim 1, wherein the support material in (a) is impregnated with a solution which contains both a compound according to the formula (IV) and a compound according to the formula (I).

3. The process according to claim 1 wherein sulphonate and mercapto groups are present in a molar ratio of 100:1 to 1:100.

4. The process according to claim 1 wherein the oxide is a member selected from the group consisting of aluminum oxide, titanium oxide, zirconium oxide and mixtures thereof.

5. The process according to claim 1 wherein the silicate is a member selected from the group consisting of natural clay and synthetically produced silicas.

6. The process according to claim 1 wherein the shape of the product is a pellet, sphere or bead.

7. The process according to claim 1 wherein $R^1$ and $R^2$ are the same and are propylene, M is H and R is H.

8. The process according to claim 1 wherein 10 to 90 mol % of the $SO_3$ groups in (I) are neutralized by alkali metal cations.

* * * * *